(12) United States Patent
Farinelli et al.

(10) Patent No.: US 11,413,092 B2
(45) Date of Patent: Aug. 16, 2022

(54) SYSTEMS AND METHODS TO FACILITATE DELIVERY OF A THERAPEUTIC AGENT INTO THE SKIN OF A SUBJECT

(71) Applicant: THE GENERAL HOSPITAL CORPORATION, Boston, MA (US)

(72) Inventors: William Farinelli, Boston, MA (US); Richard Rox Anderson, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 230 days.

(21) Appl. No.: 16/069,951

(22) PCT Filed: Jan. 9, 2017

(86) PCT No.: PCT/US2017/012699
§ 371 (c)(1),
(2) Date: Jul. 13, 2018

(87) PCT Pub. No.: WO2017/123497
PCT Pub. Date: Jul. 20, 2017

(65) Prior Publication Data
US 2019/0015155 A1  Jan. 17, 2019

Related U.S. Application Data

(60) Provisional application No. 62/278,038, filed on Jan. 13, 2016.

(51) Int. Cl.
*A61B 18/20* (2006.01)
*A61M 37/00* (2006.01)
(Continued)

(52) U.S. Cl.
CPC .......... *A61B 18/203* (2013.01); *A61K 9/0021* (2013.01); *A61M 37/00* (2013.01);
(Continued)

(58) Field of Classification Search
CPC .... A61M 37/00; A61K 9/0021; A61B 18/203; A61B 2018/00452; A61B 2018/00577; A61B 2018/2283; A61B 2217/002
See application file for complete search history.

(56) References Cited

U.S. PATENT DOCUMENTS

| 8,986,316 B1 * | 3/2015 | Jordan ............... A61B 17/1714 606/96 |
| 2005/0148567 A1 * | 7/2005 | Kjellbotn ............... A61N 5/062 514/185 |

(Continued)

OTHER PUBLICATIONS

International Search Report for Application No. PCT/US17/12699 dated Apr. 12, 2017.

*Primary Examiner* — Mallika D Fairchild
(74) *Attorney, Agent, or Firm* — Quarles & Brady LLP

(57) ABSTRACT

The present disclosure is directed to systems and methods that facilitate delivery of a therapeutic agent into the skin of a subject. A first mechanism can create a first angled channel through a first location on a surface of a subject's skin at a first angle relative to the surface of the subject's skin. A second mechanism, associated with the first mechanism, can create a second angled channel through a second location on the surface of the subject's skin at a second angle relative to the surface of the subject's skin. The first angled channel and the second angled channel intersect to form a connected channel under the surface of the subject's skin.

6 Claims, 6 Drawing Sheets

(51) Int. Cl.
  *A61K 9/00*     (2006.01)
  *A61B 18/00*    (2006.01)
  *A61B 18/22*    (2006.01)

(52) U.S. Cl.
  CPC ............ *A61B 2018/00452* (2013.01); *A61B 2018/00577* (2013.01); *A61B 2018/2283* (2013.01); *A61B 2217/002* (2013.01)

(56) References Cited

U.S. PATENT DOCUMENTS

| | | | |
|---|---|---|---|
| 2007/0239147 A1* | 10/2007 | Manstein | A61B 18/203 606/9 |
| 2008/0091184 A1* | 4/2008 | Knopp | A61B 18/14 606/31 |
| 2012/0046533 A1 | 2/2012 | Voskanyan et al. | |
| 2013/0178830 A1 | 7/2013 | Chowdhury | |
| 2014/0121587 A1 | 5/2014 | Sallberg et al. | |
| 2014/0187943 A1 | 7/2014 | Dhoke et al. | |
| 2015/0051582 A1 | 2/2015 | Pettis et al. | |
| 2015/0126913 A1* | 5/2015 | Jurna | A61B 18/12 601/9 |

\* cited by examiner

US 11,413,092 B2

SYSTEMS AND METHODS TO FACILITATE DELIVERY OF A THERAPEUTIC AGENT INTO THE SKIN OF A SUBJECT

RELATED APPLICATIONS

The present invention is a U.S. National Stage under 35 USC 371 patent application, claiming priority to Serial No. PCT/US2017/012699, filed on 9 Jan. 2017; which claims priority of U.S. Provisional Application No. 62/278,038, filed on 13 Jan. 2016, the entirety of both of which are incorporated herein by reference.

TECHNICAL FIELD

The present disclosure relates generally to systems and methods to facilitate delivery of a therapeutic agent into the skin of a subject and, more particularly, to systems and methods to facilitate delivery of a therapeutic agent into the skin of a subject by employing angled channels formed in the skin of the subject.

BACKGROUND

Drug delivery generally refers to transporting a pharmaceutical compound in the body (e.g., oral, sublingual, rectal, topical, inhalation, etc.) to safely achieve a therapeutic effect. Topical drug delivery can be defined as the application of a formulation containing the pharmaceutical compound to the skin for transportation into the body. A limiting feature for topical drug delivery is penetration of the pharmaceutical compound through the protective outer barrier of the skin, the stratum corneum. In fact, many common pharmaceutical compounds are too large to penetrate the stratum corneum.

One way to allow pharmaceutical compounds to penetrate the stratum corneum, regardless of size, is by creating small holes in the skin through the stratum corneum (e.g., with a fractional ablative laser). The resultant channels extend vertically into the tissue, thereby creating dead-end channels that the pharmaceutical compounds cannot simply and quickly migrate down. For example, the flow of pharmaceutical compounds may be limited by air bubbles and back in the dead-end channels. While general assistance techniques (e.g., massage or vibration) can be employed to aid in the delivery of pharmaceutical compounds into the channels, these techniques limit migration of the pharmaceutical compounds into the skin at an optimal concentration.

SUMMARY

The present disclosure relates generally to systems and methods to facilitate delivery of a therapeutic agent into the skin of a subject and, more particularly, to systems and methods to facilitate delivery of a therapeutic agent into the skin of a subject by employing angled channels formed in the skin of the subject.

In one aspect, the present disclosure can include a system that facilitates delivery of a therapeutic agent into the skin of a subject. The system can include a first mechanism that creates a first angled channel through a first location on a surface of a subject's skin at a first angle relative to the surface of the subject's skin. The system can also include a second mechanism, which is associated with the first mechanism and which creates a second angled channel through a second location on the surface of the subject's skin at a second angle relative to the surface of the subject's skin. The first angled channel and the second angled channel can intersect to form a connected channel under the surface of the subject's skin.

In another aspect, the present disclosure can include a method to facilitate delivery of a therapeutic agent into the skin of a subject. The method can include forming a first angled channel through a first location on a surface of a subject's skin at a first angle relative to the surface of the subject's skin. The method can also include forming a second angled channel through a second location on the subject's skin at a second angle relative to the surface of the subject's skin. The second angled channel can intersect with the first angled channel to form a connected channel under the surface of the subject's skin.

In a further aspect, the present disclosure can include a method for delivery of a therapeutic agent into the skin of a subject. The method can include delivering the therapeutic agent into a subject's skin through a connected channel formed in the subject's skin. The connected channel is formed from the intersection of two angled channels under the surface of the subject's skin.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

Definitions

Figure 1:
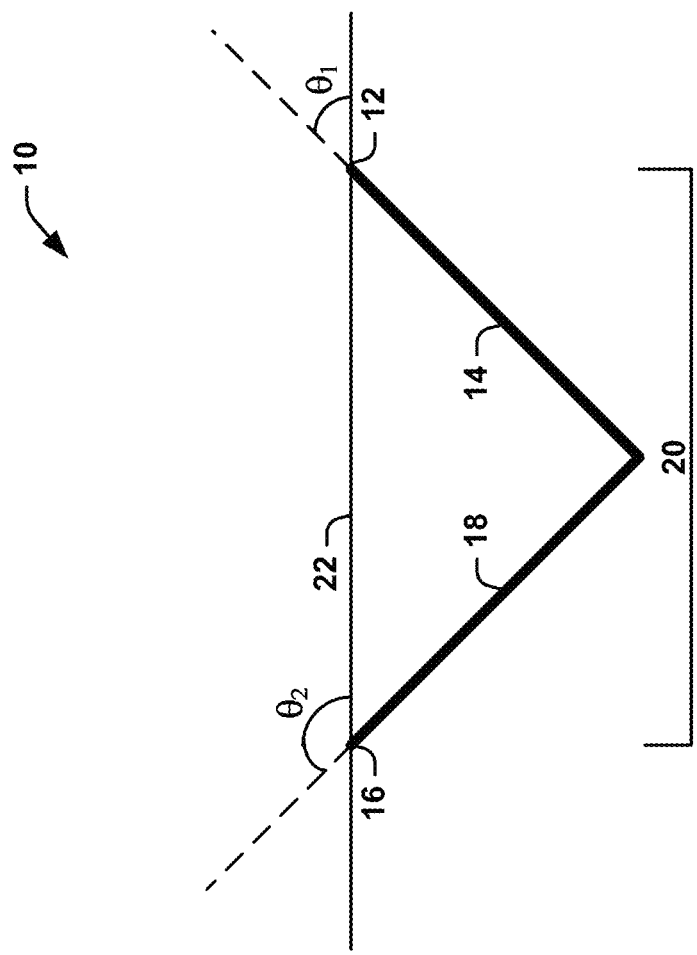
FIG. 1 is a schematic diagram illustrating a connected channel, located under a stratum corneum of a subject's skin, that can facilitate delivery of a therapeutic agent into the skin of the subject according to an aspect of the present disclosure.

Unless defined otherwise, all technical and scientific terms used herein have the same meaning as is commonly understood by one of skill in the art to which the present disclosure pertains.

In the context of the present disclosure, the singular forms "a," "an" and "the" can also include the plural forms, unless the context clearly indicates otherwise.

The terms "comprises" and/or "comprising," as used herein, can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure.

The sequence of operations (or acts/steps) is not limited to the order presented in the claims or figures unless specifically indicated otherwise.

As used herein, the term "topical drug delivery" can refer to the application of a formulation containing a therapeutic agent (e.g., a pharmaceutical compound or drug) to a subject's skin for transportation into the body. The terms "dermal drug delivery" and "trans-dermal drug delivery" can refer to entry of the therapeutic agent into the subject's skin. For example, dermal drug delivery can be a consequence of topical drug delivery.

As used herein, the term "skin" can refer to the soft outer covering of vertebrates. The skin can interface with the environment and act as the first line of defense from external factors. For example, the skin can include the epidermis (e.g., including the outermost layers of cells in the skin) and the dermis (e.g., a layer of skin between the epidermis and subcutaneous tissue that cushions the body from stress and strain).

As used herein, the term "stratum corneum" can refer to the outermost layer of the epidermis that provides a barrier layer for the subject's body. In some instances, the stratum corneum can include dead cells (corneocytes) and/or flattened cells. For example, the barrier layer can protect the underlying tissue from infection, dehydration, chemicals, mechanical stress, etc.

As used herein, the term "pharmaceutical compound" can refer to any drug used for the diagnosis, cure, treatment, or prevention of disease. The terms "pharmaceutical compound" and "drug" can be used interchangeably herein.

As used herein, the term "angled channel" can refer to an opening that at least partially extends into the skin of a subject at an angle relative to the surface of the subject's skin.

As used herein, the term "connected channel" can refer to a channel, formed beneath the surface of a subject's skin, as a result of two or more intersecting angled channels.

As used herein, the term "angle" can refer to the magnitude of the smallest rotation that maps a ray drawn along the surface of the subject's skin to a ray drawn from the entrance (or surface opening) of an angled channel in the direction of the angled channel. In one example, at least one angled channel is not normal to the surface of the skin. In another example, one angled channel can enter the subject's skin at an obtuse angle (e.g., greater than 90 degrees) and another angled channel can enter the subject's skin at an acute angle (e.g., less than 90 degrees).

As used herein, the terms "subject" and "patient" can be used interchangeably and refer to any warm-blooded organism including, but not limited to, a human being, a pig, a rat, a mouse, a dog, a cat, a goat, a sheep, a horse, a monkey, an ape, a rabbit, a cow, etc.

Overview

The present disclosure relates generally to systems and methods to facilitate delivery of a therapeutic agent into the skin of a subject and, more particularly, to systems and methods to facilitate delivery of a therapeutic agent into the skin of a subject by employing angled channels formed in the skin of the subject. Conventional techniques used to facilitate dermal drug delivery form vertical, dead-end channels in the skin. Such channels often include air bubbles, which create undesirable back pressure that prevents optimal drug delivery into the channels (and thus the skin). Advantageously, the present disclosure provides systems and methods that create two or more intersecting angled channels that form a connected channel that is free of (or can be manipulated to be free of) air bubbles, thereby minimizing or eliminating back pressure and facilitating optimal transport of therapeutic agents into the a subject's skin.

Systems

One aspect of the present disclosure can include a system for facilitating delivery of a therapeutic agent into the skin of a subject. As described in more detail below, the system can create two or more angled channels in a subject's skin. The angled channels can intersect under the surface of the subject's skin to form a connected channel. The connected channel can extend from a first opening at the surface of the subject's skin, through one or more layers of the skin, to a second opening at the surface of the subject's skin. The connected channel advantageously allows therapeutic agents (e.g., pharmaceutical compounds) to penetrate the stratum corneum and promote effective transport of the agents into the subject's skin.

FIG. 1 is a schematic diagram 10 illustrating an example of a connected channel 20, under the surface of a subject's skin 22, to facilitate delivery of a therapeutic agent into the skin of a subject. When a pharmaceutical compound is topically applied to the subject's skin 22, the connected channel 20 permits fluid flow therethrough by mitigating or eliminating back pressure created by the presence of air bubbles. The connected channel 20 can extend through, and be partially located beneath, the stratum corneum of the subject's skin. In some instances, a portion of the connected channel 20 can extend through the epidermis into the dermis. In other instances, the connected channel 20 can extend through the stratum corneum into only the epidermis of the subject's skin; in other words, the connected channel does not extend into the dermis.

Although the connected channel 20 is illustrated as having a "V" shape in FIG. 1, the connected channel can have any shape as long as it extends between a first location 12 on the surface of the subject's skin 22 and a second location 16 on the surface of the subject's skin. In some instances, the connected channel 20 can have any shape so long as at least one of the angled channels that form the connected channel extends at a non-normal angle relative to the skin 22 of the subject. In other instances, one or more of the angled channels can extend beyond the point of intersection, while, in other instances, one or more of the angled channels can end at the point of intersection.

In one aspect of the present disclosure, the connected channel 20 can be formed from a first angled channel 14 and a second angled channel 18. For example, the first angled channel 14 can intersect with the second angled channel 18 to form the connected channel 20, at least a portion of which is located under the surface of the subject's skin 22. The first angled channel 14 can enter the subject's skin (e.g., through the stratum corneum) at a first location 12. The first location 12 can include one or more points on the surface of the subject's skin 22. The first angled channel 14 can enter the subject's skin 22 at the first location 12 at a first angle ($\theta_1$) relative to the subject's skin. The second angled channel 18 can enter the subject's skin 22 (e.g., through the stratum corneum) at a second location 16 at a second angle ($\theta_2$) to the surface of the subject's skin. The second location 16 can be different than the first location 12. For example, the second location 16 can include one or more points on the surface of the subject's skin 22 that are different than the one or more points comprising the first location 12.

The first angle ($\theta_1$) and the second angle ($\theta_2$) can be selected so that the first angled channel 14 and the second angled channel 18 intersect under the surface of the subject's skin 22 to form the connected channel 20. In some instances, at least one of the first angle ($\theta_1$) and the second angle ($\theta_2$) can be non-normal relative to the surface of the subject's skin 22. In other words, at least one of the first angle ($\theta_1$) and the second angle ($\theta_2$) does not equal 90-degrees relative to the surface of the subject's skin 22. In other instances, the first angle ($\theta_1$) and the second angle ($\theta_2$) can be opposite to one another. For example, the first angle ($\theta_1$) can be an acute angle and the second angle ($\theta_2$) can be an obtuse angle. In such instances, the obtuse angle ($\theta_2$) can be at least 90-degrees greater than the acute angle ($\theta_1$). In another example, the obtuse angle ($\theta_2$) can be exactly 90-degrees greater than the acute angle ($\theta_1$). In further instances, the first angle ($\theta_1$) and the second angle ($\theta_2$) can be separated by less than 90-degrees.

A plurality of connected channels 20 can be formed under the surface of the subject's skin 22 to form a regular or irregular pattern or grid. For example, two or more connecting channels 20 can be equally spaced apart from one another at a regular interval to form a pattern. Alternatively, two or more connecting channels 20 can be spaced apart from one another at an irregular interval. As another example, two or more connected channels 20 can intersect at a common connected channel (see FIGS. 2-3).

Figure 2:
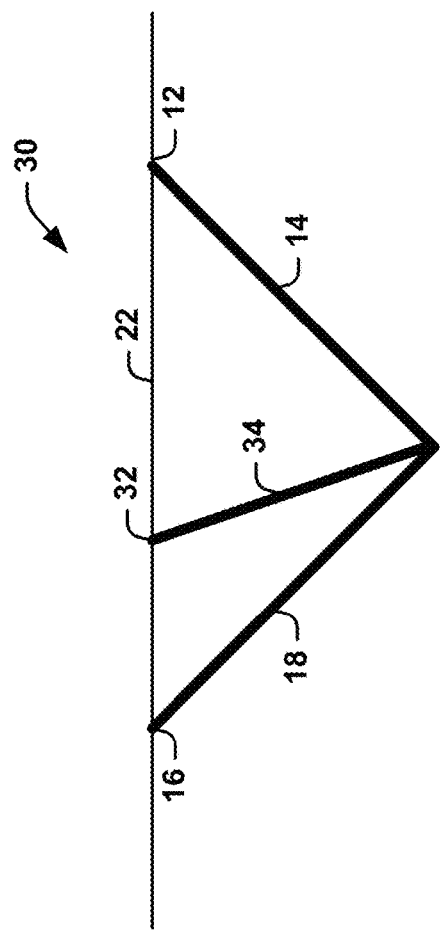
FIGS. 2-3 are schematic diagrams illustrating alternative examples of the connected channels shown in FIG. 1.

FIG. 2 is a schematic diagram 30 illustrating a third angled channel 34 comprising a connected channel 20 between the first angled channel 14 and the second angled channel 18. The third angled channel 34 can intersect the connected channel 20. As shown in FIG. 2, three intersecting and connected channels 20 can exist: (1) a connected channel between locations 12 and 16 including the first angled channel 14 and the second angled channel 18; (2) a connected channel between locations 12 and 32 including the first angled channel 14 and the third angled channel 34; and (3) a connected channel between locations 16 and 32 including the second angled channel 18 and third angled channel 34. The third angled channel 34 can be formed under the subject's skin 22 at a location 32 different than the first angled channel 14 and the second angled channel 18, and at any desired angle (e.g., a right angle, an obtuse angle, or an acute angle). In some instances, the angle of the third angled channel 34 can be different from the first angle ($\theta_1$) and/or the second angle ($\theta_2$).

Figure 3:
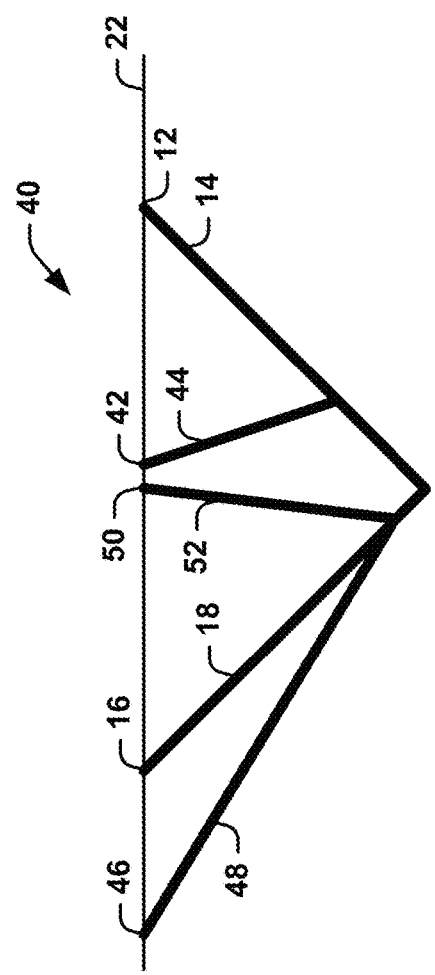

FIG. 3 is a schematic diagram 40 illustrating three angled channels 44, 48, 52 that intersect a connected channel 20 extending between the first angled channel 14 and the second angled channel 18. Similar to the third angled channel 34 in FIG. 2, angled channel 44 and angled channel 52 can also intersect the connected channel 20. Angled channel 44 can enter the subject's skin 22 at location 42, and angled channel 52 can enter the subject's skin at location 50. For example, angled channel 44 can enter the subject's skin 22 at a different angle than angled channel 52. Angled channel 48 can also intersect the connected channel 20. However, angled channel 48 can enter the subject's skin 22 at a location 46 beyond the connected channel 20 (e.g., location 46 is not between locations 12 and 16).

As shown in FIG. 3, at least nine intersecting connected channels 20 can exist: (1) a connected channel between locations 12 and 16 including the first angled channel 14 and the second angled channel 18; (2) a connected channel between locations 12 and 42 including the first angled channel 14 and angled channel 44; (3) a connected channel between locations 16 and 42 including the second angled channel 18 and angled channel 44; (4) a connected channel between locations 42 and 50 including angled channel 44 and angled channel 52; (5) a connected channel between locations 16 and 50 including the second angled channel 18 and angled channel 52; (6) a connected channel between locations 12 and 50 including the first angled channel 14 and angled channel 52; (7) a connected channel between locations 16 and 46 including the second angled channel 18 and angled channel 48; (8) a connected channel between locations 46 and 42 including angled channel 48 and angled channel 44; and (9) a connected channel between locations 12 and 46 including the first angled channel 14 and angled channel 48.

In another aspect, a connected channel 20 can be created by a system having at least one mechanism configured to form the connected channel. In one example, a single mechanism can be used to create the connected channel 20. In another example, the connected channel 20 can be created by a system comprising at least two associated mechanisms. For instance, the first mechanism can create the first angled channel 14 through a first location 12 on the surface of the subject's skin 22 at a first angle ($\theta_1$), and the second mechanism can create the second angled channel 18 through a second location 16 on the surface of the subject's skin at a second angle ($\theta_2$).

Figure 4:
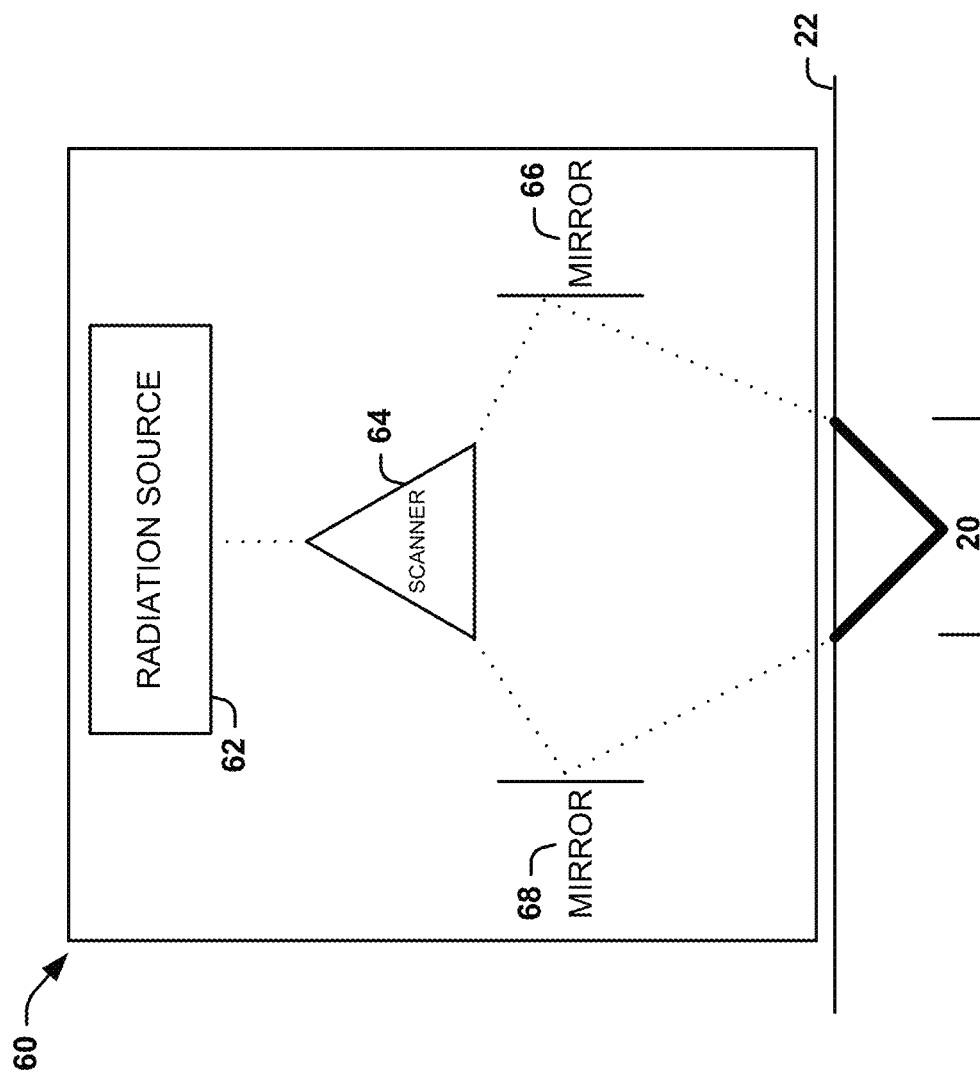
FIG. 4 is a schematic block diagram of a system, constructed in accordance with another aspect of the present disclosure, that can form the connected channel in FIG. 1 using radiation.
Figure 6:
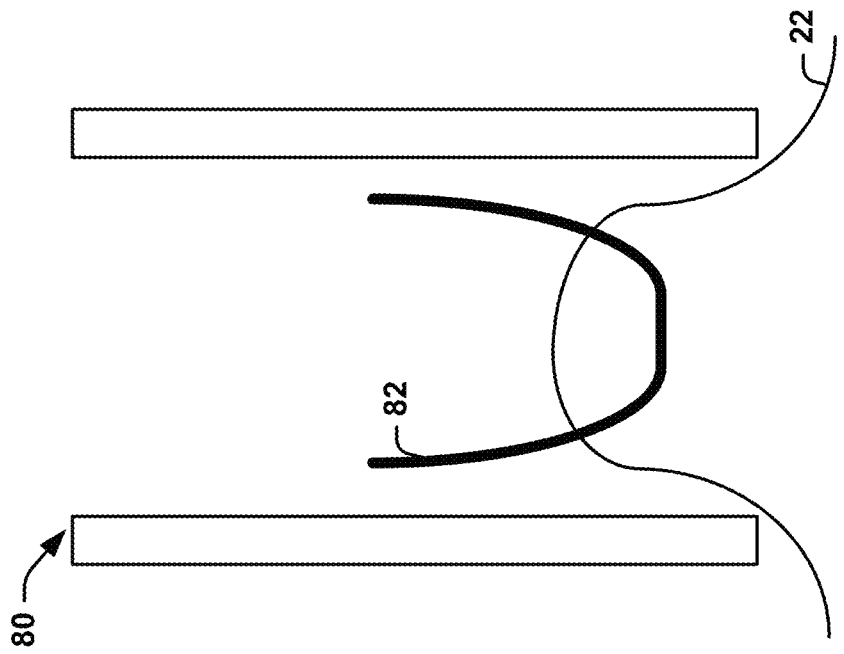
FIG. 6 is a schematic block diagram of a system, constructed in accordance with another aspect of the present disclosure, that can utilize a device to punch through a subject's skin and form the connected channel in FIG. 1.
Figure 5:
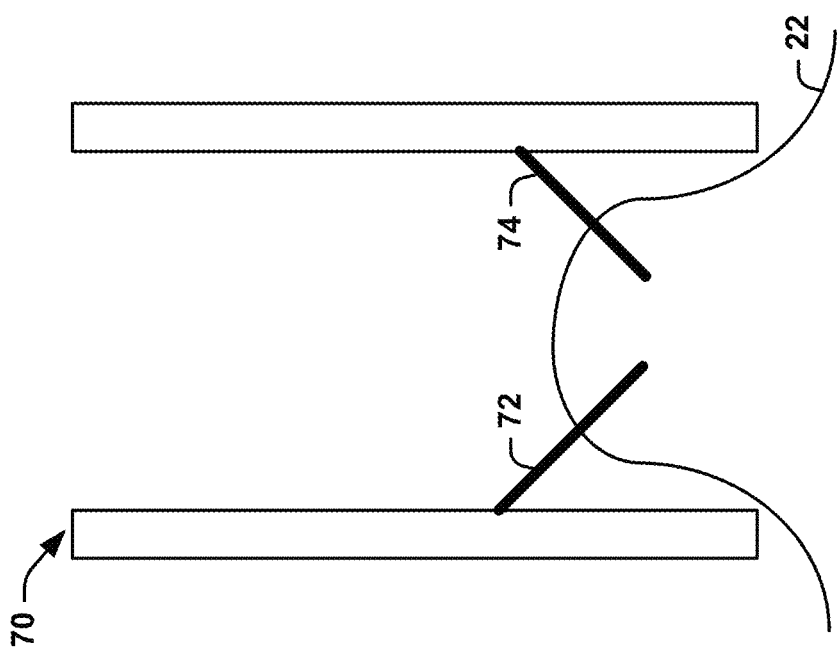
FIG. 5 is a schematic block diagram of a system, constructed in accordance with another aspect of the present disclosure, that can use coring needles to form the connected channel in FIG. 1.

Non-limiting examples of mechanisms that can be used to form the connected channel 20 can include: a light source for fractional delivery of radiation (e.g., laser light) to different areas of the subject's skin 22; sucking a portion of subject's skin into a chamber and drilling a channel (or array of channels) through the subject's skin; using coring needles to create the channels while the subject's skin is held in a vacuum chamber; and pinching or punching the subject's skin. FIGS. 4-6 illustrate different systems that can be used to form or create angled channels (e.g., first and second angled channels 14 and 18) to form a connected channel 20.

FIG. 4 shows one example of a system that can utilize fractional delivery of light to create angled channels (e.g., first and second angled channels 14 and 18) to form a connected channel 20. The system can include a housing 60, which is placed near or on the skin to deliver radiation (e.g., laser light) and thereby form the connected channel 20. The housing 60 can have any shape that is conducive to applying radiation to a subject's skin 22. The system can also include a radiation source 62 that is located within the housing 60 and configured to provide radiation. In some instances, radiation can be used for the fractional delivery of light. For example, the radiation can be a laser for providing laser light. It will be appreciated that other types of radiation can be used to create the angled channels. For example, any type of radiation with an energy sufficient to damage skin can be used.

The system can further include a scanner 64 associated with (e.g., contained within) the housing 60 and located at an output of the radiation source 62. Radiation can be emitted from the radiation source 62 and directed toward a scanner 64 configured to split the radiation into a number of radiation parts corresponding to a desired number of angled channels. The scanner 64 can separate the radiation into a plurality of beams of radiation. The beams can travel out of the scanner 64 in different directions. For example, when the radiation is laser light, the scanner 64 can separate the laser pulses to form angled channels (e.g., the first and second angled channels 14 and 18). It will be appreciated that the scanner 64 can lay down an array of laser pulses to generate any desired number and spatial orientation of angled channels and form a desired pattern or grid of angled channels.

Two mirrors 66, 68 of any shape can be located at the distal end of the scanner 64. The two mirrors 66, 68 can each be angled in a manner to create angled channels (e.g., the first and second angled channels 14 and 18). For example, one mirror 66 can be set at position A and the other mirror 68 can be set at position B. The radiation can then reflect off the mirror 66 at positions A and B to enter the skin at respective preset angles to form a connected channel 20.

FIGS. 5-6 illustrate exemplary systems that utilize suction (e.g., through suction chambers 70, 80) to facilitate formation of angled channels (e.g., first and second angled channels 14 and 18). The suction chambers 70, 80 can utilize a sufficient amount of suction or negative pressure to pull a portion of the subject's skin 22 (e.g., including the first location and/or the second location) into the chamber. In one example, the suction chambers 70, 80 can each have a wall height of about 2-3 mm. In another example, the suction chambers 70, 80 can be vacuum chambers. In some instances, the suction chambers 70, 80 can be formed of a substantially clear or opaque material. In the system of FIG. 5, needles 72, 74 are housed within the suction chamber 70. When suction is applied, the skin is pulled upward into contact with the needles 72, 74 to form the connected channel 20.

In another example of a system that utilizes suction to facilitate formation of angled channels, a coring needle 82 (which can be directly or indirectly coupled to the housing 60) can form the connected channel 20 when suction is applied within the housing. It will be appreciated that, in some instances, suction need not be applied so that the coring needle 82 can create the connected channel 20 by pinching the skin or punching through the skin (without it being pinched).

Methods

Figure 7:
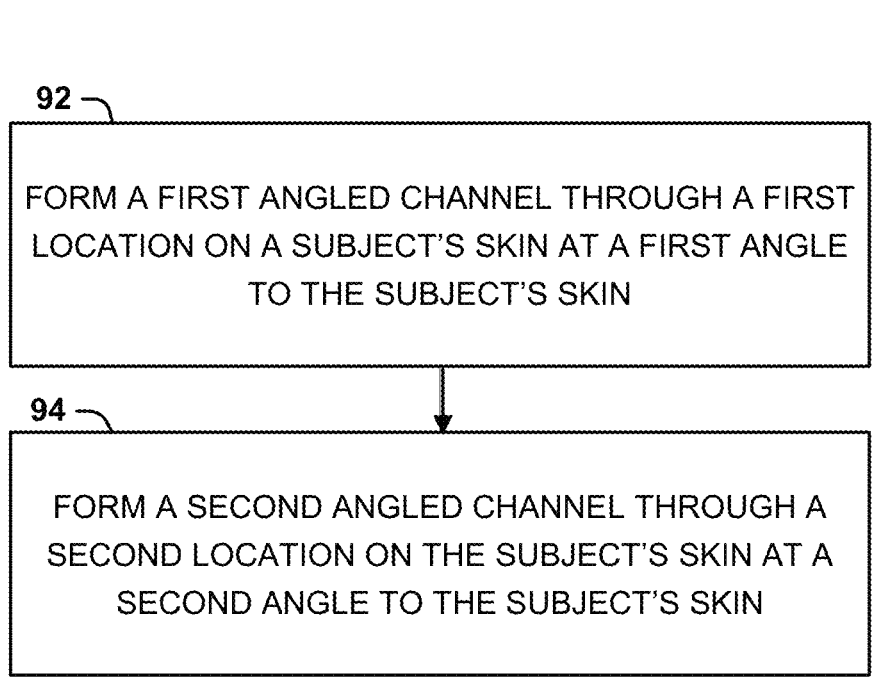
FIG. 7 is a process flow diagram illustrating a method for facilitating delivery of a therapeutic agent into the skin of a subject according to another aspect of the present disclosure.

Another aspect of the present disclosure can include a method 90 (FIG. 7) to facilitate delivery of a therapeutic agent into the skin of a subject. At 92, a first angled channel 14 can be formed at a first location 12 on a subject's skin 22 at a first angle ($\theta_1$) relative to the subject's skin. At 94, a second angled channel 18 can be formed through a second location 16 on a subject's skin at a second angle ($\theta_2$) relative to the subject's skin. The first and second angled channels 14 and 18 can be formed such that the angled channels intersect and form a connected channel 20 under the surface of the subject's skin. Techniques for forming the first and second angled channels 14 and 18 are described above.

Figure 8:
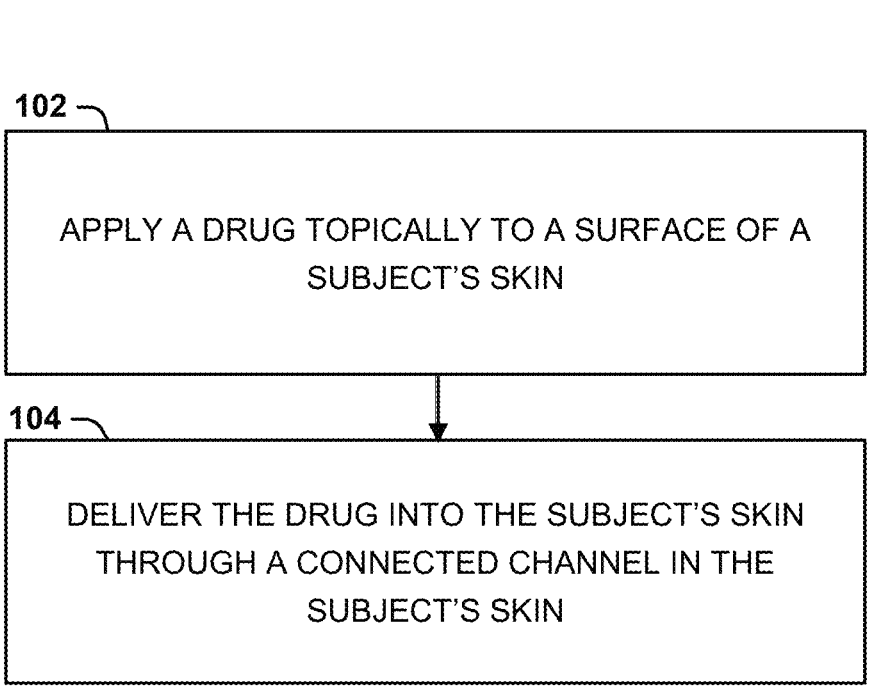
FIG. 8 is a process flow diagram illustrating a method for delivering a therapeutic agent into the skin of a subject according to another aspect of the present disclosure.

Another aspect of the present disclosure can include a method 100 (FIG. 8) for delivering a therapeutic agent into the skin of a subject. At 102, a therapeutic agent (e.g., a drug) can be applied topically to a surface of a subject's skin 22 following creation of one or more connected channels 20 (described above). At 104, the therapeutic agent can be delivered into the subject's skin through one or more of the connected channels 20. The therapeutic agent can be applied as part of a known topical formulation (e.g., a cream, ointment, gel, etc.). In instances where the therapeutic agent blocks at least one of the connected channels 20, the therapeutic agent can be removed by swiping a gloved finger, for example, over the connected channel(s).

EXAMPLE

Figure 9:
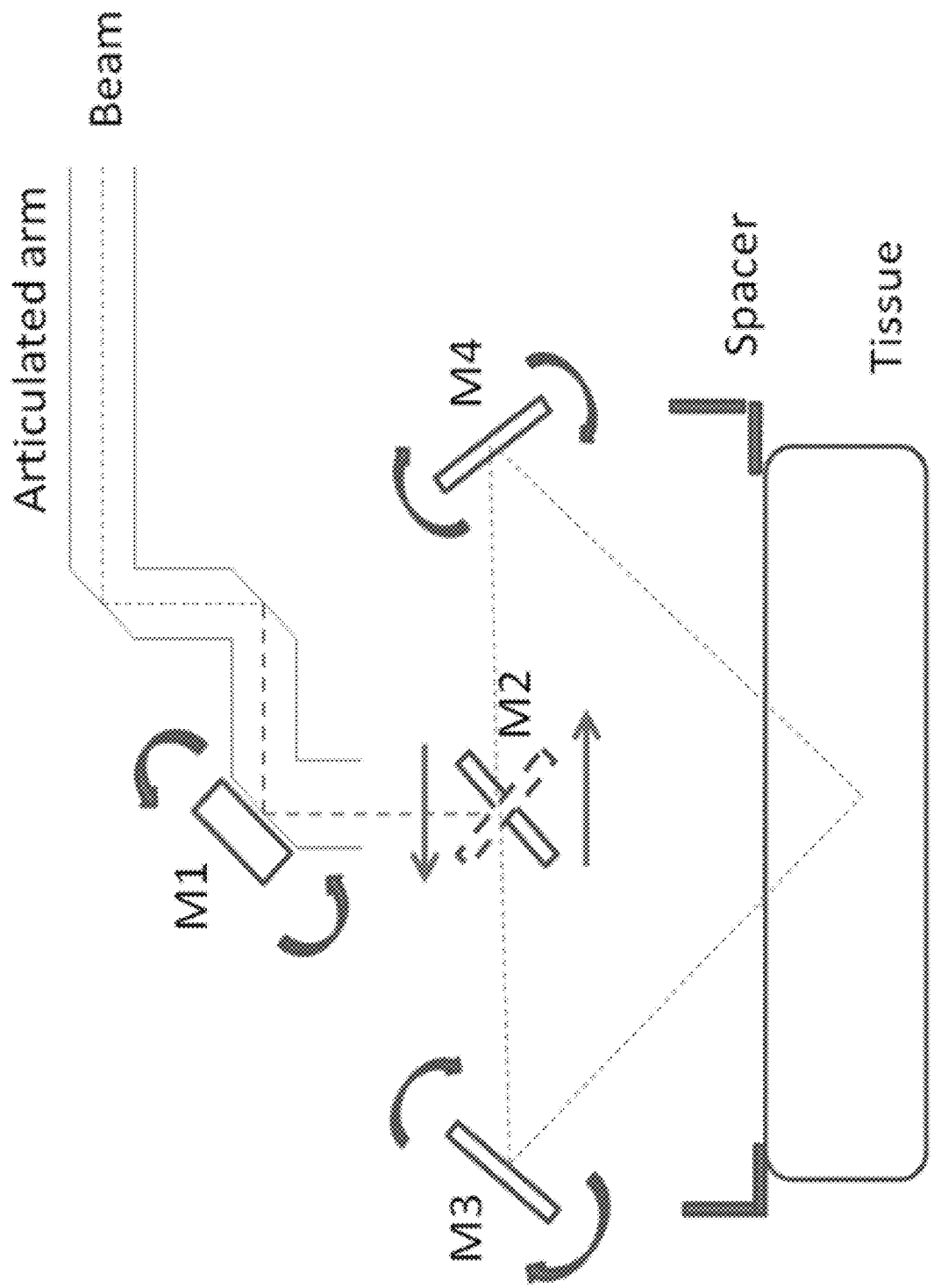
FIG. 9 is a schematic block diagram showing an example configuration of the system of FIG. 4 that can form the connected channel in FIG. 1.

FIG. 9 shows an example of a system that can be used to make the angled channels shown in FIGS. 1-3 in tissue. In this example, a standard articulated arm is used to deliver the ablative laser beam to the tissue ("beam"). The last mirror in the articulated arm is also the first mirror (M1) of a scanner unit. M1 can reflect the beam 90 degrees to the second mirror (M2) of the scanner unit. M1 can also be electromechanically driven to move the beam across M2, positioning the beam to a stationary point for some dwell time and distance and then repositioning the beam as needed or programmed.

M2 can be rotated electromechanically either to the left or to the right at approximately 45 degrees. This rotation of M2 allows the incoming 90 degree beam from M1 to reflect from M2 at 90 degrees of deflection. The beam from M2 can reflect to either mirror 3 (M3) or mirror 4 (M4), depending on the direction M2 is facing. M3 and M4 can be positioned on opposite sides of M2 and equidistant from M2. M3 and M4 can be electromechanically positioned to reflect the incoming beam from M2 downward at an angle such that M3 and M4 have identical reflective angles to cause the beams to intersect directly below M2 at some distance away. If tissue is positioned at a fixed distance away from M2 using a fixed position spacer, then the intersecting beams can create two angled channels ablated into the tissue, which can allow two holes at the surface of the tissue and at some distance from each other, to intersect at some depth within the tissue, creating a flow through channel (shown, for example, in FIG. 1).

Since M1 can be electromechanically positioned to move the beam across M2, programming M1 to move the beam to several fixed positions can allow the reflected angled beam from M3 and M4 to form an array of angled channels into the tissue with fixed spacing between each angled pair (shown, for example, in FIGS. 2-3).

From the above description, those skilled in the art will perceive improvements, changes and modifications. For example, the methods 90 and 100 are illustrated as process flow diagrams with flowchart illustrations. For purposes of simplicity, the methods 90 and 100 are shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the methods 90 and 100. Such improvements, changes and modifications are within the skill of one in the art and are intended to be covered by the appended claims.

What is claimed is:

1. A method of dermal drug delivery into skin of a subject beneath the subject's stratum corneum, the method comprising the steps of:

emitting, by a radiation source, a laser beam;

splitting, by a scanner at an output of the radiation source, the laser beam into a first portion and a second portion;

directing, by a first mirror, the first portion to a first location on the skin of the subject, the first mirror being configured to be positioned at a first angle relative to the surface of the subject's skin;

forming, by the first portion, a first channel at the first angle from the first location to a point in the skin of the subject beneath the subject's stratum corneum;

directing, by a second mirror, the second portion to a second location on the skin of the subject, different from the first location, the second mirror being configured to be positioned at a second angle different from the first angle and not normal to the surface of the subject's skin;

forming, by the second portion, a second channel at the second angle from the second location to the point to form a connected channel under the skin of the subject beneath the subject's stratum corneum by an intersection of the first channel and the second channel at the point;

applying the dermal drug to the subject's skin topically; and delivering the dermal drug into the subject's stratum corneum through the connected channel through the first angled channel and/or the second angled channel, wherein the connected channel permits fluid flow of the dermal drug within the first angled channel, the second angled channel, and the connected channel with reduced back pressure.

2. The method of claim 1, further comprising pulling the subject's skin into a vacuum chamber and forming the first angled channel and the second angled channel in the pulled skin.

3. The method of claim 1, wherein the fluid flow of the dermal drug is permitted with reduced back pressure because of the presence of fewer air bubbles in the connected channel.

4. The method of claim 1, wherein applying the dermal drug blocks at least one side of the connected channel.

5. The method of claim 4, further comprising removing the dermal drug blocking the at least one side of the connected channel by swiping the dermal drug away from the connected channel.

6. The method of claim 5, wherein the swiping is performed with at least one finger of a person.

* * * * *